United States Patent [19]

Flaugh

[11] Patent Number: 4,614,807
[45] Date of Patent: Sep. 30, 1986

[54] 6,7-DIHALOMELATONINS

[75] Inventor: Michael E. Flaugh, Indianapolis, Ind.

[73] Assignee: Eli Lilly and Company, Indianapolis, Ind.

[21] Appl. No.: 657,632

[22] Filed: Oct. 4, 1984

[51] Int. Cl.$^4$ .......................................... C07D 209/18
[52] U.S. Cl. .................................... 548/507; 548/493
[58] Field of Search ............................... 548/507, 493

[56] References Cited

U.S. PATENT DOCUMENTS

| | | | |
|---|---|---|---|
| 3,042,684 | 7/1962 | Young | 548/507 |
| 3,058,992 | 10/1962 | Allais et al. | 548/507 |
| 3,838,167 | 9/1974 | Jones | 548/493 |
| 3,947,584 | 3/1976 | Zirngibl et al. | 548/507 |
| 4,053,624 | 10/1977 | Hubner et al. | 548/493 |
| 4,087,444 | 5/1978 | Flaugh et al. | 548/507 |

OTHER PUBLICATIONS

M. A. Frohn et al, *Life Sciences*, vol. 27, pp. 2043–2046 (1980), Structure–Activity Relationship of Melatonin Analogues.

Flaugh et al., *J. Med. Chem.*, 22, 63 (1979) (Flaugh II), Synthesis and Evaluation of the Antiovulatory Activity of a Variety of Melatonin Analogues.

Ying and Greep, *Endocrinology*, 92, 333 (1973), Inhibition of Ovulation by Melatonin in the Cyclic Rat.

Chu et al., ibid, 75, 238 (1964), An Inhibitory Effect of Melatonin on the Estrous Phase of the Estrous Cycle of the Rodent.

O. Yu. Magidson, et al., *Chemical Abstracts*, 63, 18192a (1965).

*Primary Examiner*—Donald G. Daus
*Assistant Examiner*—Mary E. Ceperley
*Attorney, Agent, or Firm*—Bruce J Barclay; Arthur R. Whale

[57] ABSTRACT 6,7-Dichloromelatonin and related compounds are ovulation inhibitors of the formula

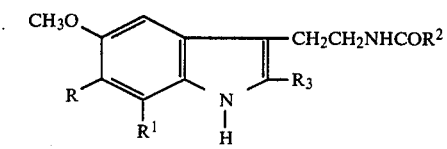

wherein R and $R^1$ are individually F or Cl, $R^2$ is $C_{1-3}$ alkyl, including methyl, ethyl, n-propyl and isopropyl, and $R^3$ is H or methyl.

4 Claims, No Drawings

6,7-DIHALOMELATONINS

BACKGROUND OF THE INVENTION

Melatonin, represented by the two-dimensional structure I below,

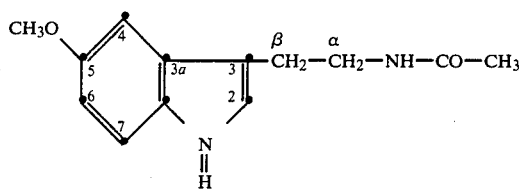

is named systematically as N-[2-(5-methoxy-3-indolyl)ethyl]acetamide. A trivial name for the same compound is N-acetyl-5-methoxytryptamine. Melatonin is a pineal gland hormone. Chu, Wortman and Axelrod, *Endocrinology*, 75, 238 (1964) inhibited both the estrous phase of the estrous cycle and ovulation in rats and mice with melatonin—see also Ying and Greep, *Endocrinology*, 92, 333 (1973).

Some substituted melatonins have been prepared. For example, Frohm et al, *Life Sci.*, 27, 2043 (1980) prepared N-acetyl 5,6-dimethoxytryptamine and also longer alkyl chain N-acyl derivatives. Flaugh and coworkers, *J. Med. Chem.*, 22, 63 (1979) prepared 6-chloro and 6-fluoromelatonin. These compounds showed increased ovulation blocking activity. α-methyl-6-chloromelatonin was also prepared, but α-methyl substitution was found to have no significant effect on ovulation-blocking activity. 6-chloromelatonin and congeners are claimed in Flaugh and Clemens, U.S. Pat. No. 4,087,444.

7-Chloromelatonin, C.A., 63, 18192a (1965) was prepared as an intermediate in the synthesis of 10-methoxy-12-chloroisodiserpidic acid via a Fischer indole synthesis from the 2-chloro-4-methoxyphenylhydrazone of 2,3-piperidinedione to yield 6-methoxy-7-chloro-1,2,3,4-tetrahydro-β-carboline. Treatment of this carboline with ethanolic potassium hydroxide gave 5-methoxy-7-chlorotryptamine-2-carboxylic acid. Decarboxylation followed by acetylation of the decarboxylated material yielded 7-chloromelatonin.

6,7-Dihalomelatonins and in particular, 6,7-dichloromelatonin, are not known. It is an object of this invention to provide such compounds via a novel synthetic method useful also in preparing 6 or 7-halomelatonins.

SUMMARY OF THE INVENTION

This invention provides compounds of the formula

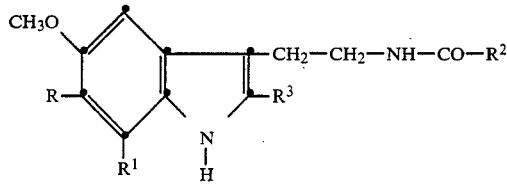

wherein R and $R^1$ are individually F or Cl, $R^2$ is $C_{1-3}$ alkyl, including methyl, ethyl, n-propyl and isopropyl, and $R^3$ is H or methyl.

Illustrative compounds falling within the scope of II include 6,7-dichloromelatonin
2-methyl-6,7-difluoromelatonin
6-chloro-7-fluoromelatonin
2-methyl-6-fluoro-7-chloromelatonin
N-propionyl-5-methoxy-6,7-dichlorotryptamine
N-isobutyryl-5-methoxy-6,7-difluorotryptamine
N-n-butyryl-2-methyl-5-methoxy-6,7-dichlorotryptamine and the like.

The compounds of this invention are prepared according to the procedure outlined in Flow Chart 1 below. This procedure is adaptable to the preparation of the known 6-halo or 7-halomelatonins and related N-acyl derivatives.

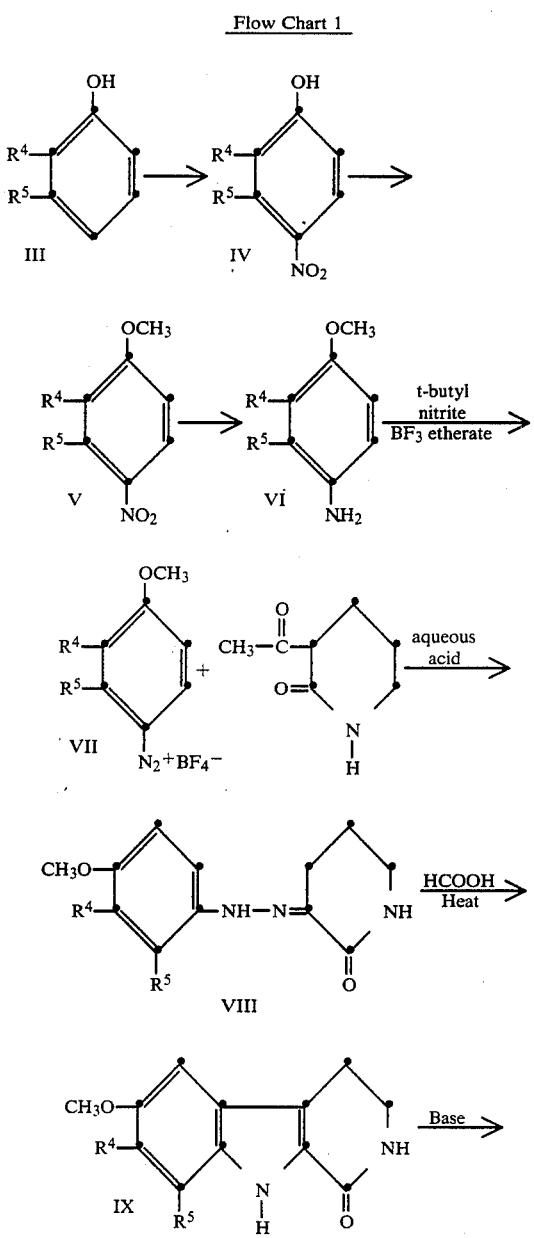

Flow Chart 1

-continued
Flow Chart 1

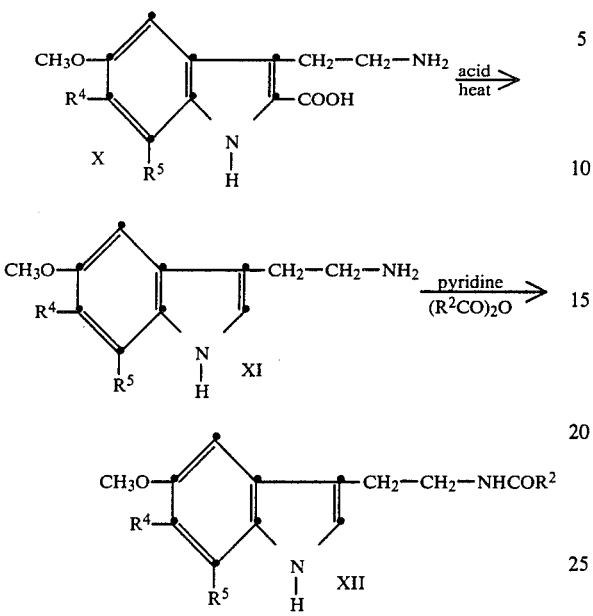

wherein $R^2$ has its previous meaning, one of $R^4$ and $R^5$ is Cl, F or H and the other is F or Cl.

In the above procedure, a halogenated phenol (III) is nitrated para to the hydroxy group to yield a 4-nitrohalophenol (IV). The phenol is then methylated to yield a 4-nitro-2 and/or 3-haloanisole (V), reduction of which yields the 4-amino derivatives (VI). The diazonium fluoroborate (VII), prepared from the amine by standard procedures, is then reacted with 3-acetyl-2-piperidone (XVII) (from Flow Chart 2) to yield a phenyl hydrazone (VIII). Heating the hydrazone with formic acid yields a 1-oxo-6-methoxy-7 and/or 8-halo-1,2,3,4-tetrahydro-9H-pyrido[3,4-b]indole (IX). Since this compound is a cyclized lactam, treatment with base yields the open-chain indole-2-carboxylic acid (X). Decarboxylation by heating in the presence of acid yields the corresponding 6-methoxy-7 and/or 8-halotryptamine (XI), acylation of which gives the desired halomelatonin (XII) or higher homologue thereof.

The above procedure not only furnishes compounds according to II above wherein both $R^4$ and $R^5$ are Cl or F, but also those known compounds in which one of $R^4$ or $R^5$ is Cl or F and the other is H; i.e., 7-chloromelatonin, 6-chloromelatonin, 7-fluoromelatonin, 6-fluoromelatonin and their higher N-acyl analogues. It will be noted that the above synthetic method yields halogenated melatonins of unambiguous structure since the preparation of the diazonium salt does not result in the production of mixtures.

The intermediate used to react with the diazonium salt (VII), 3-acetyl-2-piperidone, (XVII) is a known compound that can readily be prepared by the following procedure.

Flow Chart 2

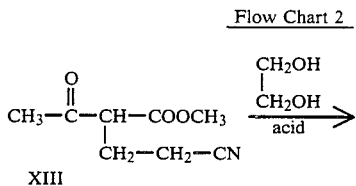

-continued
Flow Chart 2

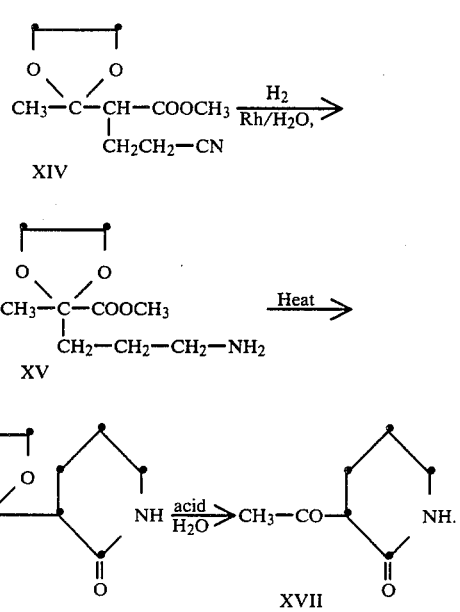

In the above procedure, XIII, prepared from methyl acetoacetate and 3-bromopropionitrile, is reacted with ethylene glycol in the presence of a catalytic amount of an acid (naphthalenesulfonic acid, p-toluenesulfonic acid or the like) in a mutual inert solvent such as toluene or benzene, to form a ketal (XIV). Hydrogenation of the ketal using a noble metal catalyst (Pt, Pd/C, Rh/Al$_2$O$_3$), preferably a supported noble metal catalyst at low hydrogen pressures (15–60 psi) produces the primary amine (XV). Cyclization of the amine to form an α-piperidone (XVI) is accomplished by heating in a mutual, inert solvent such as toluene, methylene dichloride, THF or benzene. Finally, the ketone is regenerated from the ketal by treatment with aqueous acid to produce 3-acetyl-2-piperidone (XVII).

An alternative procedure provided by this invention is particularly useful for preparing 2-methyl-6,7-dihalomelatonin although, as will be seen, it can also be used to prepare the 2-methyl-6-(or 7-)-monohalomelatonins. This synthetic procedure is delineated in Flow Chart 3 below.

Flow Chart 3

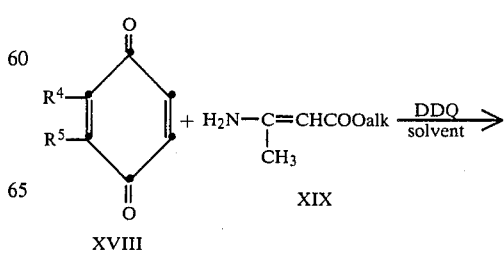

Flow Chart 3 -continued

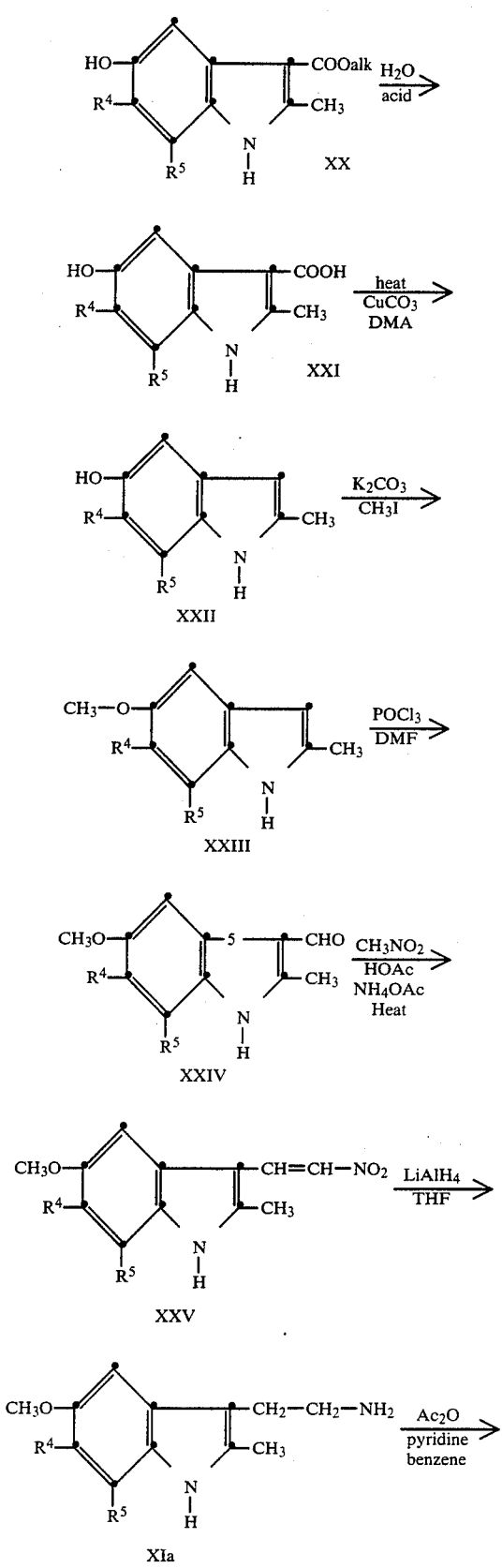

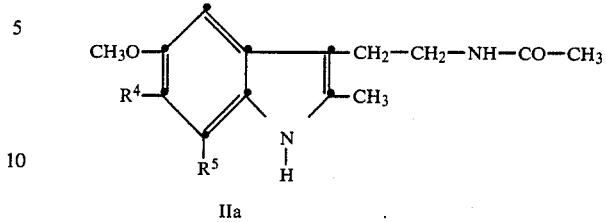

wherein one $R^4$ and $R^5$ is Cl or F and the other is H, Cl or F and alk is $C_1$–$C_4$ alkyl.

It is apparent that, if XVIII is not a symmetrical molecule; i.e., if both R and $R^1$ are not the same, two products will result on condensation with the β-aminoacrylic ester or cis or trans-p-aminorotonic ester (all represented by XIX). In this instance, there must be an added separation step at some point in the reaction scheme. On the other hand, since the reaction scheme of Flow Chart 3 yields compounds with an alpha methyl, the separation step is feasible, using HPLC. Allen et al., *J. Am. Chem. Soc.*, 88, 2536 (1966) gives procedures for the separation of substituted indole acetic acid esters like XX.

In Flow Chart 3, a mono or dihaloquinone (XVIII) is reacted with or a β-aminocrotonic ester, preferably the t-butyl ester, in a mutual inert solvent in the presence of the aromatization agent DDQ (dichlorodicyanobenzoquinone). The condensation product, XX, is a halogenated 2-methyl-5-hydroxyindolecarboxylic acid ester (with or without a 2-methyl group). The ester is hydrolysed with an acid such as p-toluenesulfonic acid to yield the corresponding free acid (XXI) which is then decarboxylated by heating in the presence of a catalytic quantity of cupric carbonate in dimethylacetamide (DPMA) or the like inert solvent. Following this step, the hydroxyl at C-5 is methylated by standard procedures (weak base, methyl iodide) to yield the 5-methoxy derivative (XXIII). Because of the presence of the acidic indole (NH), care must be taken to avoid too stringent reaction conditions under which conditions the indole nitrogen might also be methylated.

Next, the 2-methyl-5-methoxy halogenated indole (XXIII) is formylated with $POCl_3$ and dimethylformamide (DMF) to yield the 3-formyl derivatives (XXIV). Heating this compound with nitromethane in diglyme in the presence of catalytic amounts of acetic acid and potassium acetate yields the 3-(2-nitro)ethylene derivative (XXV), reduction of which with a metal hydride ($LiAlH_4$, $NaBH_4$+$AlCl_3$ or the like) in a mutual inert solvent (THF etc) yields the primary amine XIa. Acylation of XIa yields the melatonin (II where $R^2$ is methyl) or higher homologous thereof (II where $R^2$ is ethyl, n-propyl or isopropyl) substituted at C-2 with methyl.

This invention is further illustrated by the following specific examples.

EXAMPLE 1

Preparation of N-acetyl-5-methoxy-6,7-dichlorotryptamine(6,7-dichloromelatonin)

A solution of 13.2 ml of freshly distilled boron trifluoride etherate in 125 ml of methylenechloride was placed in a 1 liter 3-neck round bottom flask equipped with nitrogen inlet tube and stirrer. The solution was chilled below about 0° C. Next, a solution of 13.7 g of 4-amino-2,3-dichloroanisole and 65 ml of methylenechloride was added thereto over a 20 minute period with vigorous stirring. A solution of 10.6 ml of t-butyl nitrite and 65 ml of methylenechloride was added dropwise over a 30 minute period to the reaction mixture. After the addition had been completed the reaction mixture was kept below about 0° C. with stirring for about 40 minutes, at which time 375 ml of pentane were added to desolubilize 4-methoxy-2,3-dichlorophenyldiazoniumfluoroborate formed in the above reaction. The diluted reaction mixture was stirred for an additional hour and then filtered. The filter cake, comprising the diazonium salt, was dried in vacuo to yield a white powder melting at 153°–154° C. with decomposition.

The diazonium salt obtained in the above procedure was dissolved in a mixture of 166 ml of acetic acid and 60 ml of water and 5 g of 3-acetyl-2-piperidone were added. The reaction mixture was stirred for about 30 minutes during which time a precipitate formed after which 77 ml of water were added. The reaction mixture was stirred for an additional hour after which time it was refrigerated for about 2 hours. A precipitate formed, comprising 3-(4-methoxy-2,3-chlorophenylhydrazono)-2-piperidone, which was collected by filtration, and the filter cake washed with water. After drying, 8.46 g of yellow crystals melting at 219°–220° C. with decomposition were obtained; molecular ion by mass spectrum at 301 (M-1 peak).

Analysis Calc.: C, 47.70; H, 4.34; N, 13.91; Cl, 23.47; Found: C, 47.86; H, 4.46; N, 13.62; Cl, 23.65.

A suspension of 8.22 g of the above hydrazone in 210 ml of 80% formic acid was prepared. The suspension was heated about 20 minutes at about 100° C., thus dissolving the hydrazone. An additional 20 ml of 99% formic acid were added. A precipitate started to form almost immediately. Heating was continued for about an hour, after which time the reaction mixture was refrigerated for several hours. The precipitate was collected by filtration, and the filter cake washed with water. 6.97 g of an orange product, comprising 1-oxo-6-methoxy-7,8-dichloro-1,2,3,4-tetrahydro-9H-pyrido[3,4-b]indole were obtained. The precipitate was recrystallized from a mixture of ethanol and acetone. Two crops of crystalline 1-oxo-6-methoxy-7,8-dichloro-1,2,3,4-tetrahydro-9H-pyrido[3,4-b]indole were obtained melting at about 263°–264° C.

Analysis Calc.: C, 50.55; H, 3.54; N, 9.82; Cl, 24.87; Found: C, 50.52; H, 3.72; N, 9.58; Cl, 24.61. NMR (DMSO-$d_6$) $\delta$ at 2.94 (t, J=6Hz, 2H, 5-CH$_2$; 3.52 (t, J=6Hz, 2H, 4-CH$_2$); 3.92 (s, 3H, OCH$_3$); 7.28 (s, 1H, 6-H); 7.68 (s, 1H, N—H); 11.90 (s, 1H, N—H).

The above lactam was hydrolyzed with base according to the following procedure: 5 g of 1-oxo-6-methoxy-7,8-dichloro-1,2,3,4-tetrahydro-9H-pyrido[3,4-b]indole were dissolved in a mixture of 77 ml of ethanol and 51 ml of water. 13.9 g of potassium hydroxide were added, and the solution was heated to refluxing temperature overnight under a nitrogen atmosphere. The reaction mixture was cooled, and the pH adjusted to about 4 by the addition of 12N aqueous hydrochloric acid. A precipitate formed in the acidic solution, which precipitate was isolated by filtration, and the filter cake washed with water. 5.15 g of 3-(2-aminoethyl)-5-methoxy-6,7-dichloroindol-2-carboxylic acid were obtained. The compound melted at 248°–249° C.

NMR (DMSO-$d_6$/TFA-$d_1$) $\delta$ at 3.07 (br mult., 2H, $\beta$-CH$_2$); 3.29 (br mult., 2H, $\alpha$-CH$_2$); 3.92 (s, 3H, OCH$_3$); 7.38 (s, 1H, 4-H); 7.92 (br, H, N—H); 9.72 (br s, 2H, N—H).

The indolecarboxylic acid from the previous preparation was decarboxylated by heating with 140 ml of 3N aqueous hydrochloric acid under vigorous reflux for about 48 hours. The starting carboxylic acid was insoluble in the aqueous acidic mixture but the product of the decarboxylation 6-methoxy-7,8-dichlorotryptamine was soluble therein.

Upon cooling the reaction mixture, a portion of the hydrochloride salt of the tryptamine precipitated. Water was added to redissolve the salt. The solution was filtered to remove a small quantity of an insoluble impurity. The pH of the acidic aqueous filtrate was adjusted to about pH=12 with concentrated aqueous sodium hydroxide. A product, comprising 5-methoxy-6,7-dichlorotryptamine, precipitated. The mixture was refrigerated. The product was isolated by filtration from the chilled reaction mixture. 3.31 g of a grayish powder melting at about 181°–184° C. were obtained. Recrystallization of a portion of this precipitate from aqueous ethanol yielded grayish brown platelets of 5-methoxy-6,7-dichlorotryptamine melting at about 189°–192° C.

Analysis Calc.: C, 50.99; H, 4.67; N, 10.81; Cl, 27.36; Found: C, 51.08; H, 4.73; N, 11.05; Cl, 27.16.

NMR (acetone-$d_6$/DMSO-$d_6$) $\delta$ at 1.70 (br s, 1H, N—H); 1.90 (br s, 1H, N—H); 2.96 (t, J=10Hz, 2H, $\beta$-CH$_2$); 3.49 (t, J=10 Hz, $\alpha$-CH$_2$); 3.91 (s, 3H, OCH$_3$); 7.20 (s, 1H, 2-H); 7.27 (s, 1H 4-H).

Three grams of 5-methoxy-6,7-dichlorotryptamine were dissolved in 24 ml of toluene and 6 ml of pyridine. The solution was chilled to about 0° C., and 3 ml of acetic anhydride were added. The reaction mixture was allowed to warm to ambient temperature where it was stirred for about 3 hours. The volatile constituents were removed from the reaction mixture in vacuo, and the residue dissolved in chloroform. The chloroform solution was extracted successively with 1 N aqueous hydrochloric acid, saturated aqueous sodium bicarbonate and brine. The organic solution was dried, and the solvent removed therefrom in vacuo to yield grayish brown crystals which were recrystallized from a toluene/hexane solvent mixture to yield 3.01 g of 6,7-dichloromelatonin melting at about 168° C.

Analysis Calc.: C, 51.84; H, 4.69; N, 9.30; Cl, 23.54; Found: C, 52.10; H, 4.40; N, 9.33; Cl, 23.34.

NMR (DMSO-$d_6$) $\delta$ at 1.79 (s, 3H, CO—CH$_3$); 2.80 (t, J=8Hz, 2H, $\beta$-CH$_2$); 3.32 (qt, J's=7+8Hz, 2H, $\alpha$-CH$_2$); 3.87 (s, 3H, OCH$_3$); 7.22 (s, 2H, 2-H+4-H); 7.90 (t, J=7Hz, 1H, N—H); 11.12 (br s, 1H, N—H).

By using 3-chloro-4-methoxyaniline or 2-chloro-4-methoxyaniline in place of 2,3-dichloro-4-methoxyaniline in the above reaction sequence, one can prepare 6-chloromelatonin or 7-chloromelatonin.

EXAMPLE 2

Preparation of 2-methyl-6,7-dichloromelatonin

A reaction mixture was prepared from 10 g of 2,3-dichlorobenzoquinone and 8.9 g of t-butyl 2-aminocrotonate in 400 ml of chloroform. The reaction mixture rapidly turned purple. 1.0 g of (DDQ) 2,3-dichloro-5,6-dicyanobenzo-1,4-benzoquinone was added, and the reaction mixture heated to reflux temperature for about an hour. The reaction temperature was cooled to ambient temperature, and the chloroform removed in vacuo. The residue containing t-butyl 2-methyl-5-hydroxy-6,7-dichloroindole-3-carboxylate was dissolved in acetone. The acetone solution was filtered, and the acetone removed from the filtrate in vacuo. Chromatography of the resulting residue over silica gel (activity III), using benzene as the eluant, yielded fractions containing the desired t-butyl 2-methyl-5-hydroxy-6,7-dichloroindole-3-carboxylate which fractions were combined, the solvent removed therefrom, and the resulting residue recrystallized from a benzene/hexane solvent mixture. Yellow-tan crystals melting at about 188°-191° C. were obtained; yield=22%.

Analysis Calculated: C, 53.18; H, 4.78; N, 4.43; Cl 22.43; Found: C, 53.41; H, 5.02; N, 4.22; Cl 22.65.

NMR (DMSO-$d_6$) δ at 1.60 (s, 9H, t-Bu); 2.68 (s, 3H, 2-CH$_3$); 7.62 (s, 1H, 4-H); 10.00 (s, 1H, N—H); 11.92 (br, s, 1H, O—H).

A solution was prepared from 7.48 g of the above ester and 500 ml of benzene under a nitrogen blanket. 500 mg of p-toluenesulfonic acid monohydrate were added, and the resulting mixture heated to reflux temperature for about 1.75 hours. The reaction mixture was cooled, and the precipitate, comprising 2-methyl-5-hydroxy-6,7-dichloroindole-3-carboxylic acid, was recrystallized from methanol/water to yield 5.20 g of crystals melting at about 238°-242° C.

Analysis Calculated: C, 46.35; H, 2.33; N, 5.41; Cl 27.37; Found: C, 46.23; H, 2.30; N, 5.52; Cl 27.15.

NMR (DMSO-$d_6$) δ at 2.69 (s, 3H, 2-CH$_3$); 7.64 (s, 1H, 4-H); 10.00 (br s, 1H, NH); 12.83 (br s, 1H, (O—H).

A solution was prepared by dissolving 1.53 g of the above carboxylic acid in about 25 ml of N,N-dimethylacetamide (DMA). A small amount of cupric carbonate was added, and the mixture heated to reflux temperature for about ¾ of an hour in order to decarboxylate the free acid. The reaction mixture was allowed to cool, and the cooled reaction mixture poured into water. The aqueous mixture was extracted several times with benzene. The benzene extracts were combined, and combined extracts were washed several times with brine and then dried. Removal of the solvent yielded a residue which was purified by chromatography over silica gel (activity III), using benzene as the eluant. Fractions containing the desired decarboxylated product, 2-methyl-5-hydroxy-6,7-dichloroindole, were combined, and the solvent removed therefrom; crude weight=1.26 g. This residue was dissolved in a small amount of methanol, and water was added to the point of an incipient precipitation. The crystallization mixture was cooled, and crystals of 2-methyl-5-hydroxy-6,7-dichlorindole formed thereby were separated by filtration; yield=64.6%; mp=135°-136° C.

Analysis Calculated: C, 50.03; H, 3.27; N, 6.48; Cl 23.82; Found: C, 50.26; H, 3.32; N, 6.53; Cl 32.88.

NMR (DMSO-$d_6$) δ at 2.38 (s, 3H, 2-CH$_3$); 6.08 (s, 1H, 2-H); 6.97 (s, 1H, 4-H); 9.59 (s, 1H, N—H); 11.03 (s, 1H, O—H).

The next step in this synthetic procedure is the preparation of the methyl ether of 2-methyl-5-hydroxy-6,7-dichloroindole. A more expeditious procedure, however, is to combine the decarboxylation step and the preparation of the methyl ether without isolating the intermediate phenol. This combined reaction procedure was carried out as follows: 5.5 g of 2-methyl-5-hydroxy-6,7-dichloroindole-3-carboxylic acid were dissolved in 80 ml of DMA. A small quantity of cupric carbonate was added, and the reaction mixture heated to reflux temperature for about 1 hour under a nitrogen blanket. The reaction mixture was then cooled, and 3.52 g of potassium carbonate were added, followed by 6.0 g of methyl iodide. This reacton mixture was stirred at 55°-60° C. for about 4 hours and was then allowed to remain at ambient temperature with stirring for 3 days. The reaction mixture was next poured into cold water, and an insoluble product, 2-methyl-5-methoxy-6,7-dichloroindole collected by filtration. In addition, the mother liquor from the filtration was extracted with methylene chloride. The methylene chloride extract was separated, and the methylene chloride removed therefrom in vacuo. The residue was washed with water, and the water washes discarded. This residue plus the above precipitate were combined and subjected to sublimation. The sublimed product was recrystallized from hexane. 2-methyl-5-methoxy-6,7-dichloroindole thus prepared melted at 96°-98° C. 2.54 g of colorless needles were obtained.

Analysis Calculated: C, 52.20; H, 3.94; N, 6.09; Cl 30.82; Found: C, 52.01; H, 3.91; N, 5.88; Cl 30.73.

NMR (CDCl$_3$) δ at 2.43 (s, 3H, 2-CH$_3$); 3.88 (s, 3H, OCH$_3$); 6.17 (br s, 1H, 2-H); 6.95 (s, 1H, 4-H); 7.98 (br s, 1H, N—H).

Next, the 2-methyl-5-methoxy-6,7-dichloroindole was formylated according to the following procedure: 3.6 ml of dimethylformamide were added slowly in dropwise fashion to 1.04 ml of phosphorus oxychloride. The temperature was maintained in the range 10°-20° C. After the addition had been completed, the reaction mixture was allowed to stand for about 15 minutes whereupon 2.50 g of 2-methyl-5-methoxy-6,7-dichloroindole in 1.5 ml of DMF were added. The reaction mixture solidified. Additional DMF was added. The reaction mixture was stirred for about an hour at about 33° C. and then was poured over crushed ice. 2 g of sodium hydroxide and 8.3 ml of water were added slowly. The solution was maintained slightly acidic by means of vigorous agitation using a pH meter to monitor the acidity during the first half of the addition of the aqueous sodium hydroxide. After the entire quantity of aqueous sodium hydroxide had been added, the mixture was heated to reflux temperature and stirred at that temperature for about 1 hour. The reaction was then cooled. Crystals which had precipitated were separated by filtration. The precipitate was triturated with methanol, and the methanol discarded. The precipitate was then dried. 2-methyl-3-formyl-5-methoxy-6,7-dichloroindole thus prepared was a mustard colored powder melting at 264°-267° C. with decomposition; total yield=89%.

Analysis Calculated: C, 51.19; H, 3.51; N, 5.43; Cl 27.47; Found: C, 51.34; H, 3.24; N, 5.55; Cl 27.55.

NMR (CDCl$_3$/DMSO-$d_6$) δ at 2.71 (s, 3H, 2-CH$_2$); 3.93 (s, 3H, OCH$_3$); 7.71 (s, 1H, 4-H); 10.09 (s, 1H, CHO); 11.65 (br s, 1H, N—H).

The 3-formyl derivative prepared as above was next condensed with nitromethane in the presence of ammonium acetate as follows: 2.35 g of 2-methyl-3-formyl-5-methoxy-6,7-dichloroindole were added slowly to 20 ml of nitromethane plus 10 ml of diglyme. 500 mg of ammonium acetate were added plus about 3 drops of acetic acid. This reaction mixture was heated to reflux temperature under a nitrogen blanket overnight. A solid precipitate, comprising 2-methyl-3-(2-nitrovinyl)-5-methoxy-6,7-dichloroindole formed in the above reaction, was separated by filtration. The filter cake was recrystallized from aqueous acetic acid to yield a yellow powder melting at about 280°-283° C.; yield=78%.

Analysis Calculated: C, 47.86; H, 3.35; N, 9.30; Cl 23.55; Found: C, 47.58; H, 3.41; N, 9.07; Cl 23.60.

NMR (DMSO-$d_6$) δ at 2.56 (s, 3H, 2-$CH_3$); 3.96 (s, 3H, $OCH_3$); 7.29 (s, 1H, 4-H); 7.91 (d, J=13 Hz, 1H, β-H); 8.23 (d, J=13 Hz, 1H, α-H).

The above nitrovinyl compound was reduced with lithium aluminum hydride according to the following procedure: 8.2 g of lithium aluminum hydride were stirred with 235 ml of tetrahydrofuran (THF) under a nitrogen blanket. 10.67 g of 18M sulfuric acid were added to 43 ml of THF which was cooled to about 0° C. during the addition. This solution was added to the lithium aluminum hydride mixture. Next, a solution of 2.20 g of 2-methyl-3-(2-nitrovinyl)-5-methoxy-6,7-dichloroindole in 43 ml of THF was added thereto in dropwise fashion at ambient temperature over a period of about 1.25 hours. The reaction mixture was stirred for an additional 1.25 hours, and was then diluted with ice, followed by the addition of cold 20% aqueous sodium hydroxide. Chloroform was added to the mixture, and the chloroform extract separated. The chloroform extraction process was repeated, and the chloroform extracts combined and dried. Removal of the solvent yielded a residue comprising 2-methyl-5-methoxy-6,7-dichlorotryptamine formed in the above reaction. The residue was dissolved with difficulty in hot boiling ethyl acetate. The ethyl acetate solution was cooled, and hexane added to the point of incipient precipitation. The recrystallization mixture was then chilled. Crystalline 2-methyl-5-methoxy-6,7-dichlorotryptamine thus formed was collected by filtration. The crystals melted at about 228°-230° C. Total yield, including second crop material, was 73%.

Analysis Calculated: C, 52.76; H, 5.17; N, 10.26; Cl 25.96; Found: C, 52.50; H, 5.14; N, 9.94; Cl 26.25.

NMR (DMSO-$d_6$) δ at 2.33 (s, 3H, 2-$CH_3$); 2.69 (s, 4H, α-$CH_2$+β-$CH_2$); 3.84 (s, 3H, $OCH_3$); 7.10 (s, 1H, 4-H); 11.0 (br s, 1H, N—H).

The above tryptamine was acetylated by the procedure of Example 1 to yield, 6,7-dichloromelatonin. Yield in the acetylation step was 96%; mp=184°-186° C.

Analysis Calculated: C, 53.35; H, 5.12; N, 8.89; Cl 22.50; Found: C, 53.09; H, 4.88; N, 8.76; Cl 22.31.

NMR (CDCl$_3$) δ at 1.90 (s, 3H, CO—$CH_3$); 2.37 (s, 3H, 2-$CH_3$); 2.85 (t, J=7 Hz, 2H, β-$CH_2$); 3.45 (qt, J=7 Hz, 2H, α-$CH_2$); 3.91 (s, 3H, $OCH_3$); 6.94 (s, 1H, 4-H); 7.33 (s, 2H, N—H's).

EXAMPLE 3

Preparation of 2,3-dichloro-p-anisidine

A solution was prepared from 200 g of 2,3-dichlorophenol and 540 ml of glacial acetic acid. The solution was cooled, and a solution of 58 ml of 90% nitric acid in 160 ml of glacial acetic acid was added in dropwise fashion with stirring to the solution of the phenol. After half of the solution of the phenol had been added, the reaction mixture was allowed to warm to ambient temperature. It was stirred for 15 minutes at ambient temperature after all of the dichlorophenol had been added. The reaction mixture was then poured over 3,000 ml of an ice/water mixture. The yellowish product which precipitated was collected. The product was heated in a sublimation apparatus over a 4 day period at 80° C. at 4 torr. to remove any 2-nitro-5,6-dichlorophenol formed as a by-product in the above nitration. The residue was recrystallized from toluene to yield 80.3 g of 4-nitro-2,3-dichlorophenol; m.p.=148°-150° C.

Analysis Calculated: C, 34.65; H, 1.45; N, 6.73; Found: C, 34.72; H, 1.47; N, 6.55.

NMR (CDCl$_3$) δ at 6.18 (s, 1H, O—H); 7.05 (d, J=9 Hz, 1H, 6-H); 7.87 (d, J=9 Hz; 1H, 5-H).

The above phenol was converted to the corresponding methyl ether by a Williamson synthesis, in which the phenol was dissolved in DMF and solid potassium carbonate added to the solution. After this reaction mixture had been stirred for 1 hour, methyl iodide was added (following the procedure of Example 2). The reaction was heated at about 55° C. for about 7 hours. The reaction mixture was poured onto 3 liters of ice. The product of the reaction, 4-nitro-2,3-dichloroanisole precipitated, and was collected by filtration. Yield=71.0%. The crystallization from toluene gave tan crystals melting at about 84°-85° C.

Analysis Calculated: C, 37.87; H, 2.27; N, 6.31; Found: C, 37.67; H, 2.34; N, 6.37.

Mass spectrum molecular ion at 221 (M-1 peak).

The above methyl ether was reduced with Raney Nickel in ethanol solution to yield 4-methoxy 2,3-dichloroaniline (2,3-dichloro-p-anisidine). The hydrogenation was carried out at 60 psi over a 7 hour period. The catalyst was removed by filtration, and the solvent evaporated from the filtrate to yield a residue which, on being recrystallized from ethanol/water, gave a 79% yield of 2,3-dichloro-p-anisidine. The hydrochloride salt was prepared in ether; m.p.=216° C. (with decomposition).

Analysis Calculated: C, 36.79; H, 3.53; N, 6.13; Found: C, 36.94; H, 3.48; N, 6.37.

EXAMPLE 4

Preparation of 3-Acetyl-2-piperidone

A mixture of 108 g of methyl 2-(2-cyanoethyl) acetoacetate, 50 ml of ethyleneglycol, 500 ml of toluene, and 500 mg of 1-naphthalenesulfonic acid was heated for 3.5 hours at reflux in an apparatus equipped with a Dean-Stark trap. At this point, nmr carried out on an aliquot of the cooled reaction mixture from which the solvent had been stripped, showed about 20% starting material. Another 10 ml of ethyleneglycol were added and the reaction mixture refluxed for a few additional hours. The reaction mixture was treated successively with saturated aqueous sodium bicarbonate and brine and was then dried. The toluene was removed by evaporation in vacuo, and the residue distilled. An 89% yield of ethyl 2-(2-cyanoethyl) acetoacetate ethyleneketal boiling at 154°-159° at 4 torr. was obtained.

The above ketal was hydrogenated over a rhodium-on-alumina catalyst as follows: After dissolving 16 g of ethyl 2-(2-cyanoethyl)acetoacetate ethyleneketal in 90 ml of 10% ethanolic ammonia, 2 g of 5% rhodium-on-alumina were added, and the mixture hydrogenated at low pressure. The catalyst was separated by filtration, and the solvent removed from the filtrate to yield, as a residue, ethyl 2-(3-aminopropyl)acetoacetate ethyleneketal formed in the above hydrogenation. NMR indicated a mixture of the expected ketal plus some cyclized product produced by the next reaction step. The crude product from the above reaction was therefore heated in toluene solution for about 2 hours to convert the amino derivative to 3-acetyl-2-piperidone ethyleneketal. NMR showed the reaction being incomplete at this point; heating in toluene was therefore continued for 7 more hours. NMR again showed incomplete reaction; so heating was continued overnight. After a total of 24 hours of heating under reflux, the reaction mixture was cooled, and the solvent was removed in vacuo.

The ketal group was removed from the above crude product by heating in 100 ml of 1N aqueous sulfuric acid for 3 hours. 3-Acetyl-2-piperidone, formed the above reaction, was extracted with several portions of chloroform. The chloroform extracts were combined, and the combined extracts washed with saturated aqueous sodium bicarbonate. The combined extracts were dried, and the solvent removed in vacuo. A product which crystallized through the aid of a small amount of carbon tetrachloride, was isolated by filtration. A 40% yield of 3-acetyl-2-piperidone based on starting nitrile was obtained; m.p.=101°-103° C. [reported 96°-100° C. by Ploner et al., Ber., 100, 1675 (1967)].

The compounds of the invention are ovulation inhibitors, with a longer duration of action than the monochloromelatonins. The degree of ovulation inhibitory activity was determined according to the following protocol.

Adult female rats with regular estrus cycles of four days each are employed. The estrus cycle consists of 2 days of diestrus followed by a day of proestrus and then a day of estrus. Daily vaginal smears were recorded, and rats were selected after they had demonstrated at least two consecutive 4-day estrus cycles. On the afternoon of proestrus, luteinizing hormone (LH) is released into the blood by the pituitary gland. The LH travels to the ovary where it induces ovulation, resulting in the presence of eggs in the oviduct on the day of estrus.

The test compound is administered orally at predetermined times on the day of proestrus. The rat is sacrificed on the following day (estrus). The oviduct is removed and examined microscopically for the presence of ova. The absence of ova indicates that the compound is active in blocking ovulation.

Table 1 below gives the results of one of these experiments. In the Table, column 1 gives the name of the compound, column 2 the time of administration and column 3 the percent inhibition of ovulation.

TABLE 1

| Name of Compound | Time of Administration | Percent Inhibition of ovulation |
| --- | --- | --- |
| 6-chloro-melatonin | 10:00 a.m. | 0 |
| 6,7-dichloro-melatonin | 10:00 a.m. | 100 |
| 2-methyl-6,7-dichloromelatonin | 8:00 a.m. | 100 |

As can be seen from the data presented in Table 1, the two dichloromelatonins of this invention have a longer duration of action than the monochloromelatonin.

As ovulation inhibitors, the compounds of this invention can be used as contraceptive or population control agents in mammals. Their oral activity renders them particularly useful in achieving contraception and population control, particularly of unwanted (in their present numbers) mammalian species.

For example, the compounds of this invention can be formulated in combination with baits and/or attractants and placed in feeding stations accessible to undesirable rodents and other small animals including Canidae such as coyotes, foxes, jackals, and wild dogs; and birds, such a starlings, gulls, redwing blackbirds, pigeons, and the like, to greatly reduce the population thereof. They can also be used to reduce hazards to aviation by lessening the presence of birds and animals on runways in the vicinity of air fields. They also can be used to reduce the population of undesirable birds and animals so as to aid in the prevention and the spread of disease, and to reduce the destruction of property in both rural and urban areas.

The compounds of this invention can be administered as such, or they can be compounded and formulated into pharmaceutical preparations in unit dosage form for oral or parenteral administration. In the compounding or formulation, organic or inorganic solids and/or liquids which are pharmaceutically acceptable carriers can be employed. Suitable such carriers will be well recognized by those of ordinary skill in the art. The oral compositions may take the form of tablets, powder granules, capsules, suspensions, solutions, and the like.

The compounds of this invention, when administered in an effective amount will inhibit ovulation and therefore conception in birds and mammals. The usual daily dose is from about 0.02 milligrams to about 20 milligrams per kilogram body weight of the recipient. The preferred daily dose is from about 1 milligram to about 8 milligrams per kilogram body weight of the recipient.

I claim:

1. A compound of the formula

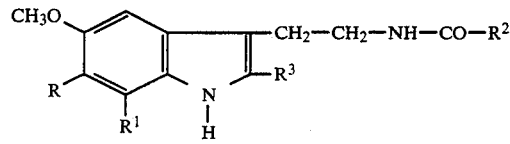

wherein both R and $R^1$ are Cl, $R^2$ is $C_{1-3}$ alkyl and $R^3$ is H or methyl.

2. A compound according to claim 1, said compound being 6,7-dichloromelatonin.

3. A compound according to claim 1, said compound being 2-methyl-6,7-dichloromelatonin.

4. A compound of the formula

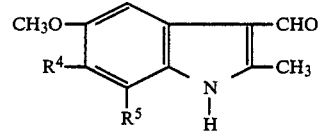

wherein both $R^4$ and $R^5$ are Cl.

* * * * *